United States Patent [19]

Sommer et al.

[11] Patent Number: 4,540,816

[45] Date of Patent: Sep. 10, 1985

[54] SINGLE-VESSEL PROCESS FOR PREPARING RING-SUBSTITUTED N-ALKYLANILINES

[75] Inventors: Karl Sommer, Königstein; Rudolf Schickfluss, Kelkheim, both of Fed. Rep. of Germany

[73] Assignee: Hoechst Aktiengesellschaft, Fed. Rep. of Germany

[21] Appl. No.: 608,979

[22] Filed: May 10, 1984

[30] Foreign Application Priority Data

May 13, 1984 [GB] United Kingdom ............... 3317470

[51] Int. Cl.$^3$ ............... C07C 102/04; C07C 102/06; C07C 102/02; C07C 102/00
[52] U.S. Cl. ............................................. 564/218
[58] Field of Search ........................................ 564/218

[56] References Cited

U.S. PATENT DOCUMENTS 3,857,886 12/1974 Hensel et al. ............... 564/218 X
3,919,269 11/1975 Jaffe et al. ................... 564/218 X
3,960,886 6/1976 Schulenberg ................ 564/218 X
4,144,270 3/1979 Neri et al. ..................... 564/218

Primary Examiner—Paul F. Shaver
Attorney, Agent, or Firm—Connolly and Hutz

[57] ABSTRACT

Process for preparing ring-substituted N-alkylanilines of the formula (1)

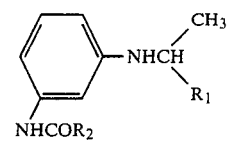

in which $R_1$ and $R_2$ each denote methyl or ethyl, in a single vessel, which comprises acylating m-nitroaniline in an excess of an aliphatic carbonyl compound of the formula (2)

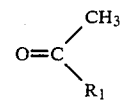

in which $R_1$ is as defined above, with an acylating agent which contains the —CO—$R_2$ acyl radical—which is transferred— and reductively alkylating the resulting compound of the formula (3)

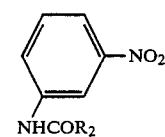

in which $R_2$ is as defined above, at temperatures of 120°–160° C. under a hydrogen pressure of 20–150 bar without intermediate isolation through the presence of an acid reaction promoter and of a nickel catalyst.

5 Claims, No Drawings

SINGLE-VESSEL PROCESS FOR PREPARING RING-SUBSTITUTED N-ALKYLANILINES

The present invention relates to a process for preparing ring-substituted N-alkylanilines by reductive alkylation of ring-substituted nitrobenzenes without intermediate isolation (single-vessel process).

It has been found that ring-substituted N-alkylanilines of the general formula (1)

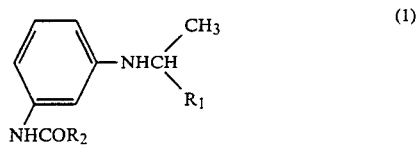

in which $R_1$ and $R_2$ each denote methyl or ethyl, can be prepared in good yields in an environmentally acceptable manner using a single-vessel process in which m-nitroaniline is acylated in an excess of an aliphatic carbonyl compound of the general formula (2)

in which $R_1$ is as defined above, with an acylating agent which contains the —CO—$R_2$ acyl radical—which is transferred—and the resulting compound of the general formula (3)

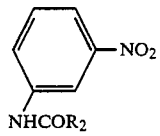

in which $R_2$ is as defined above, is reductively alkylated at temperatures of 120°–160° C., preferably at 130°–150° C., and under a hydrogen pressure of 20–150 bar, preferably 50–100 bar, to a compound of the general formula (1) without intermediate isolation through the presence of an acid reaction promoter and of a nickel catalyst.

The reaction takes between 4 and 7 hours in an autoclave.

The acylating agent can be acetyl chloride, propionyl chloride or, preferably, acetic anhydride or propionic anhydride.

The acid reaction promoter can be a lower saturated fatty acid, such as, for example, formic acid, acetic acid or propionic acid, benzene sulfonic acid or a toluene sulfonic acid. If the acylating agent used in the process according to the invention is acetic anhydride or propionic anhydride, acetic acid and propionic acid respectively are released in the course of the acylation and act as acid reaction promoters, so that in these cases there is no need for the separate addition of an acid reaction promoter.

Suitable nickel catalysts are preferably partially stabilized supported (on charcoal or alumina) nickel catalysts with an approximately 50% nickel content.

When the reaction has ended, the catalyst is separated off by filtration, and the reaction mixture is vacuum-distilled. The residue of the distillation, which is an approximately 70% strength melt, can immediately be further processed as it is into a dyestuff or can be precipitated in the form of a compound of the formula (1) by adding water or aqueous salt solutions.

The ring-substituted N-alkylanilines of said formula (1) can be prepared in a single-vessel process without intermediate isolation from the simple m-nitroaniline via the reaction stages of acylation, reduction and reductive alkylation, the overall yield for the 3 stages being about 85%. This simple and economical process makes it possible to prepare the claimed coupling components in an environmentally acceptable manner without the use of carcinogenic alkylating agents, such as diethyl sulfate, ethylene oxide or acrylonitrile.

German Offenlegungsschrift No. 2,745,552 describes a process for preparing ring-substituted N-alkylanilines which differ structurally from those obtainable using the process according to the invention in that they carry unbranched aliphatic substituents on the aniline nitrogen and an additional substituent in the ortho-position relative to the substituted amino group and are prepared by reacting already acylated nitrobenzene compounds at between 20° and 100° C. in an inert polar solvent with an aldehyde in the presence of hydrogen and hydrogenating catalysts. Compared with this existing process, the process according to the invention has the advantage that the reductive alkylation is also possible with the more inert ketones which serve as both solvent and participant in the reaction.

EXAMPLE 1

107 parts by weight of acetic anhydride are added dropwise at about 50° C. to a solution of 138 parts by weight of m-nitroaniline in 800 parts by volume of methyl ethyl ketone. The mixture is then stirred at said temperature for 2 hours.

The resulting suspension is reductively alkylated at 135° C. under a hydrogen pressure of about 100 bar in the course of 6 hours after flushing with nitrogen in a 2-liter autoclave using 20 parts by weight of a nickel catalyst.

The reaction solution obtained is filtered with suction to remove the catalyst, and the solvent is distilled off under reduced pressure. The melt thus obtained, which is almost all 1-isobutylamino-3-acetylaminobenzene (melting point 66° C.), can be used as it is as a coupling component for preparing azo dyestuffs by dissolving it in dilute sulfuric acid.

EXAMPLE 2

137 parts by weight of propionic anhydride are added dropwise at about 50° C. to a solution of 138 parts by weight of m-nitroaniline in 800 parts by volume of acetone, and the rest of the procedure is as described in Example 1, affording a melt which is almost all 1-isopropylamino-3-propionylaminobenzene (melting point 67° C.) and which can again be used as it is as a coupling component for preparing azo dyestuffs by dissolving it in dilute sulfuric acid.

What is claimed is:
1. A process for preparing ring-substituted N-alkylanilines of the formula (1)

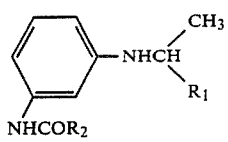 (1)

in which $R_1$ and $R_2$ each denote methyl or ethyl, in a single vessel, which comprises acylating m-nitroaniline in an excess of an aliphatic carbonyl compound of the formula (2)

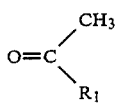 (2)

in which $R_1$ is as defined above, with an acylating agent which contains the —CO—$R_2$ acyl radical—which is transferred—and reductively alkylating the resulting compound of the formula (3)

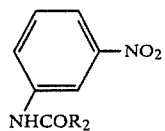 (3)

in which $R_2$ is as defined above, at temperatures of 120°–160° C. under a hydrogen pressure of 20–150 bar without intermediate isolation through the presence of an acid reaction promoter and of a nickel catalyst.

2. The process as claimed in claim 1, wherein the acylating agent is acetic anhydride or propionic anhydride.

3. The process as claimed in claim 1, wherein the acid reaction promoter is a lower saturated fatty acid.

4. The process as claimed in claim 1, wherein the reductive alkylation is carried out at temperatures of 130°–150° C. under a hydrogen pressure of 50 to 100 bar.

5. The process as claimed in claim 1, wherein the nickel catalyst is a partially stabilized supported nickel catalyst having an approximately 50% nickel content.

* * * * *